(12) United States Patent
Kurahara

(10) Patent No.: US 9,562,918 B2
(45) Date of Patent: Feb. 7, 2017

(54) SAMPLE RACK CONVEYING UNIT AND AUTOMATIC ANALYSIS SYSTEM

(71) Applicant: JEOL Ltd., Tokyo (JP)

(72) Inventor: Rui Kurahara, Tokyo (JP)

(73) Assignee: JEOL Ltd., Tokyo (JP)

( * ) Notice: Subject to any disclaimer, the term of this patent is extended or adjusted under 35 U.S.C. 154(b) by 0 days.

(21) Appl. No.: 14/821,993

(22) Filed: Aug. 10, 2015

(65) Prior Publication Data
US 2016/0047833 A1 Feb. 18, 2016

(30) Foreign Application Priority Data
Aug. 13, 2014 (JP) .................................. 2014-164667

(51) Int. Cl.
| | | |
|---|---|---|
| G01N 35/02 | (2006.01) | |
| G01N 35/04 | (2006.01) | |
| B65G 19/02 | (2006.01) | |
| B65G 1/02 | (2006.01) | |

(52) U.S. Cl.
CPC ............. *G01N 35/026* (2013.01); *B65G 19/02* (2013.01); *B65G 1/02* (2013.01); *B65G 2201/0261* (2013.01); *G01N 2035/0415* (2013.01); *G01N 2035/0484* (2013.01)

(58) Field of Classification Search
CPC .......................... G01N 2035/0484; B65G 1/02
See application file for complete search history.

(56) References Cited

U.S. PATENT DOCUMENTS

| | | | | | |
|---|---|---|---|---|---|
| 4,692,308 | A | * | 9/1987 | Riley | ............... G01N 35/021 422/562 |
| 5,088,591 | A | * | 2/1992 | Grecksch | ............... B65H 67/06 198/465.1 |
| 7,434,678 | B1 | * | 10/2008 | Kitazumi | ............... B65G 15/02 198/465.3 |

FOREIGN PATENT DOCUMENTS

JP    61427 A1    1/1994

* cited by examiner

*Primary Examiner* — P. Kathryn Wright
(74) *Attorney, Agent, or Firm* — The Webb Law Firm

(57) ABSTRACT

A sample rack conveying unit 30 includes a sliding rail plate 53, a presser 66, a first guide plate 55, and a second guide plate 56. The sliding rail plate 53 has a groove portion 71 formed along a track on which a sample rack 90 slides and along which the sample rack 90 is conveyed. The presser 66 passes through the groove portion 71 and presses the sample rack 90. The first guide plate 55 is arranged on an outer side of a curved portion in a radial direction. The second guide plate 56 is arranged on an inner side of the curved portion in the radial direction.

5 Claims, 6 Drawing Sheets

SAMPLE RACK CONVEYING UNIT AND AUTOMATIC ANALYSIS SYSTEM

BACKGROUND OF THE INVENTION

Field of the Invention

The present invention relates to a sample rack conveying unit for conveying a sample rack in which a sample container is accommodated and an automatic analysis system having this sample rack conveying unit.

Description of Related Art

Conventionally, an automatic analyzing device for quantitatively measuring a specific substance in a sample which is a biological specimen such as blood or urine has been known. In the automatic analyzing device, a sample container for accommodating (holding and transporting) a sample, is used. In this type of automatic analyzing device, a sample accommodating unit in which, for example, a plurality of the sample containers is accommodated and a reaction unit for causing the sample and a reagent to react with each other are provided.

Furthermore, a sample rack conveying unit for conveying the sample container to the sample accommodating unit of the automatic analyzing device is known. The sample rack conveying unit conveys the plurality of sample containers in a state of being accommodated in the sample rack.

A technology described in Japanese Patent Laid-Open No. 6-1427 describes a device provided with a first rack conveying conveyor for linearly advancing the sample rack to a first direction, a second rack conveying conveyer for linearly advancing the sample rack to a second direction different from the first direction, and a disc for rotating the sample rack. In the technology described in Japanese Patent Laid-Open No. 6-1427, a direction in which the sample rack is conveyed is changed from the first direction to the second direction, by sequentially conveying the sample rack in order of the first rack conveying conveyer, the disc, and the second rack conveying conveyer.

SUMMARY OF THE INVENTION

However, with the technology described in Japanese Patent Laid-Open No. 6-1427, three driving portions are required in order to drive the first rack conveying conveyer, the second rack conveying conveyer, and the disc. Therefore, there is a problem in which the number of components is increased by the driving portions, thereby not only increasing costs but also complicating a mechanism for conveying the sample rack.

In consideration of the aforementioned problems, an object of the present invention is to provide a sample rack conveying unit and an automatic analyzing system, which can reduce the number of the driving portions and can simplify the mechanism for conveying the sample rack.

In order to solve the aforementioned problems and to achieve the object of the present invention, a sample rack conveying unit of the present invention includes a sliding rail plate, a presser, an endless driving belt, a plurality of pulleys, a driving portion, a first guide plate, and a second guide plate. The sliding rail plate has a groove portion formed along a track on which a sample rack for accommodating a sample container slides and along which the sample rack is conveyed. The presser passes through the groove portion and presses the sample rack. The presser is mounted on the driving belt. The driving belt is stretched across the plurality of pulleys. The driving portion rotationally drives the plurality of pulleys. The first guide plate is arranged on an outer side of a curved portion in a radial direction where a direction of the track on which the sample rack is conveyed changes, and guides conveyance of the sample rack. The second guide plate is arranged on an inner side of the curved portion in the radial direction, and guides conveyance of the sample rack.

Furthermore, an automatic analysis system of the present invention includes an automatic analyzing device for analyzing a sample accommodated in the sample container and the aforementioned sample rack conveying unit for conveying the sample rack in which the sample container is accommodated.

According to the sample rack conveying unit and the automatic analysis system of the present invention, the number of driving portions can be reduced, and a mechanism for conveying the sample rack can be simplified.

DESCRIPTION OF THE INVENTION

Figure 1:
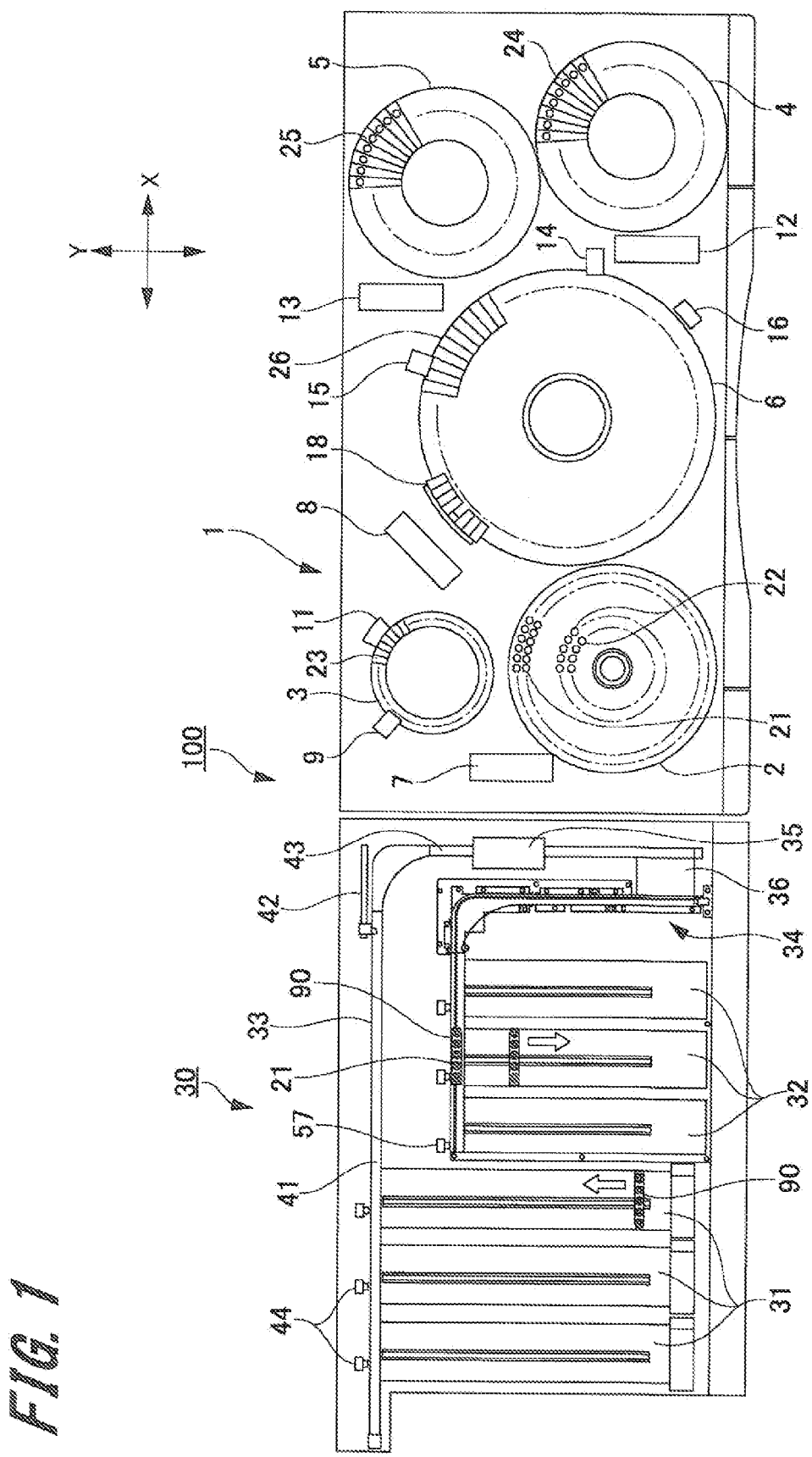
FIG. 1 is a plan view schematically illustrating an automatic analysis system according to an exemplary embodiment of the present invention.

An exemplary embodiment of a sample rack conveying unit and an automatic analysis system of the present invention will be described by referring to FIGS. 1 to 9. Note that, in each drawing, the same reference numerals are attached to common members. Furthermore, the description will be made in the following order, but the present invention is not necessarily limited to the following form.

Exemplary Embodiment 1-1. Configuration of Automatic Analysis System

First, an automatic analysis system according to an exemplary embodiment of the present invention (hereinafter referred to as "this embodiment") will be described by referring to FIG. 1.

FIG. 1 is an explanatory view schematically illustrating the automatic analysis system of this embodiment.

A device illustrated in FIG. 1 is a biochemical analysis system 100 applied as an example of the automatic analysis system of the present invention. The biochemical analysis system 100 is a device for automatically measuring an amount of a specific, component contained in a biological specimen such as blood or urine.

As illustrated in FIG. 1, the biochemical analysis system 100 has a biochemical analyzing device 1 for automatically measuring an amount of a specific component contained in a biological specimen and a sample rack conveying unit 30 for conveying a sample rack.

1-2. Configuration of Biochemical Analyzing Device

The biochemical analyzing device 1 includes a sample turntable 2, a dilution turntable 3, a first reagent turntable 4, a second reagent turntable 5, and a reaction turntable 6. Furthermore, the biochemical analyzing device 1 includes a sample dilution pipette 7, a sampling pipette 8, a dilution agitation device 9, a dilution cleaning device 11, a first reagent Pipette 12, a second reagent pipette 13, a first reaction agitation device 14, a second reaction agitation device 15, a multi-wavelength photometer 16, and a reaction container cleaning device 18.

The sample turntable 2 illustrating an example of a sample accommodating unit of this embodiment is formed in a substantially cylindrical container shape with one end in an axial direction open. A plurality of sample containers 21 and a plurality of dilution liquid containers 22 are accommodated in this sample turntable 2. A sample made of blood, urine or the like is accommodated in the sample container 21. A special dilution liquid other than a physiological saline which is an ordinary dilution liquid is accommodated in the dilution liquid container 22.

The plurality of sample containers 21 is arranged side by side at predetermined intervals in a circumferential direction of the sample turntable 2. Furthermore, the sample containers 21 arranged side by side in the circumferential direction of the sample turntable 2 are set in two rows at a predetermined interval in a radial direction of the sample turntable 2.

The plurality of dilution liquid containers 22 is arranged on an inner side of the sample turntable 2 in the radial direction than the row of the plurality of sample containers 21. The plurality of dilution liquid containers 22 is arranged side by side at predetermined intervals in the circumferential direction of the sample turntable 2 in the same way as the plurality of sample containers 21. Then, the dilution liquid containers 22 arranged side by side in the circumferential direction of the sample turntable 2 are set in two rows at a predetermined interval in the radial direction of the turntable 2.

Note that arrangement of the plurality of sample containers 21 and the plurality of dilution liquid containers 22 is not limited to two rows, but may be one row or may be arranged in three rows or more in the radial direction of the sample turntable 2.

The sample turntable 2 is rotatably supported along the circumferential direction by a driving mechanism not shown. Then, the sample turntable 2 is rotated at a predetermined speed by each predetermined angle range in the circumferential direction by the driving mechanism not shown. Furthermore, the dilution turntable 3 is arranged in the periphery of the sample turntable 2.

Each of the dilution turntable 3, the first reagent turntable 4, the second reagent turntable 5, and the reaction turntable 6 is formed in a substantially cylindrical container shape with one end in the axial direction open in the same way as the sample turntable 2. The dilution turntable 3 and the reaction turntable 6 are rotated at a predetermined speed in each predetermined angle range in the circumferential direction thereof by the driving mechanism not shown. Note that the reaction turntable 6 is set so as to be rotated by a semicircle or more by one movement.

In the dilution turntable 3, the plurality of dilution containers 23 is accommodated side by side in the circumferential direction of the dilution turntable 3. The sample suctioned from the sample container 21 arranged on the sample turntable 2 and diluted (hereinafter referred to as a "diluted sample") is accommodated in the dilution container 23.

In the first reagent turntable 4, the plurality of first reagent containers 24 is accommodated side by side in the circumferential direction of the first reagent turntable 4. Furthermore, in the second reagent turntable 5, the plurality of second reagent containers 25 is accommodated side by side in the circumferential direction of the second reagent turntable 5. Then, a concentrated first reagent is accommodated in the first reagent container 24, and a concentrated second reagent is accommodated in the second reagent container 25.

Moreover, the first reagent turntable 4, the first reagent container 24, the second reagent turntable 5, and the second reagent container 25 are held at a predetermined temperature by a cooling mechanism not shown. Therefore, the first reagent accommodated in the first reagent container 24 and the second reagent accommodated in the second reagent container 25 are cooled at a predetermined temperature.

The reaction turntable 6 illustrating an example of a reaction unit of this embodiment is arranged among the dilution turntable 3, the first reagent turntable 4, and the second reagent turntable 5. In the reaction turntable 6, the plurality of reaction containers 26 is accommodated side by side in the circumferential direction of the reaction turntable 6. The diluted sample sampled from the dilution container 23 of the dilution turntable 3, the first reagent sampled from the first reagent container 24 of the first reagent turntable 4, and the second reagent sampled from the second reagent container 25 of the second reagent turntable 5 are poured into the reaction container 26. Then, in this reaction container 26, the dilution sample, the first reagent, and the second reagent are agitated, and reaction is caused.

The sample dilution pipette 7 is arranged in the periphery of the sample turntable 2 and the dilution turntable 3. The sample dilution pipette 7 is movably supported in an axial direction (for example, vertical direction) of the sample turntable 2 and the dilution turntable 3 by a dilution pipette driving mechanism not shown. Furthermore, the sample dilution pipette 7 is turnably supported by the dilution pipette driving mechanism along a horizontal direction substantially in parallel to openings of the sample turntable 2 and the dilution turntable 3. Then, the sample dilution pipette 7 makes a reciprocating motion between the sample turn table 2 and the dilution turntable 3 by rotationally moving along the horizontal direction. Note that, when the sample dilution pipette 7 moves between the sample turntable 2 and the dilution turntable 3, the sample dilution pipette 7 passes through the cleaning device not shown.

Here, an operation of the sample dilution pipette 7 will be described.

When the sample dilution pipette 7 moves to a predetermined position above the opening in the sample turntable 2, the sample dilution pipette 7 lowers along the axial direction of the sample turntable 2, and a pipette provided at its tip end is inserted into the sample container 21. At this time, the sample dilution pipette 7 suctions a predetermined amount of the sample accommodated in the sample container 21 by operation of a sampling pump not shown. Subsequently, the sample dilution pipette 7 rises along the axial direction of the sample turntable 2 and withdraws the pipette from inside the sample container 21. Then, the sample dilution pipette 7 rotationally moves along the horizontal direction and moves to the predetermined position above the opening in the dilution turntable 3.

Next, the sample dilution pipette 7 lowers along the axial direction of the dilution turntable 3 and inserts the pipette into the predetermined dilution container 23. Then, the sample dilution pipette 7 discharges the suctioned sample and a predetermined amount of the dilution liquid (for example, physiological saline) supplied from the sample dilution pipette 7 itself, into the dilution container 23. As a result, the sample is diluted to a predetermined times of concentration in the dilution container 23. After that, the sample dilution pipette 7 is cleaned by the cleaning device.

The sampling pipette 8 is arranged between the dilution turntable 3 and the reaction turntable 6. The sampling pipette 8 is supported capable of movement and rotational movement in the axial direction (vertical direction) of the dilution turntable 3 and in the horizontal direction in the same way as the sample dilution pipette 7 by a sampling pipette driving mechanism not shown. Then, the sampling pipette 8 makes a reciprocating motion between the dilution turntable 3 and the reaction turntable 6.

This sampling pipette 8 inserts the pipette into the dilution container 23 of the dilution turntable 3 and suctions a predetermined amount of the dilution sample. Then, the sampling pipette 8 discharges the suctioned dilution sample into the reaction container 26 of the reaction turntable 6.

The first reagent pipette 12 is arranged between the reaction turntable 6 and the first reagent turntable 4, and the second reagent pipette 13 is arranged between the reaction turntable 6 and the second reagent turntable 5. The first reagent pipette 12 is supported capable of movement and rotational movement in the axial direction (vertical direction) and the horizontal direction of the reaction turntable 6 by the first reagent pipette driving mechanism not shown. Then, the first reagent pipette 12 makes a reciprocating motion between the first reagent turntable 4 and the reaction turntable 6.

The first reagent pipette 12 inserts the pipette into the first reagent container 24 of the first reagent turntable 4 and suctions a predetermined amount of the first reagent. Then, the first reagent pipette 12 discharges the suctioned first reagent into the reaction container 26 of the reaction turntable 6.

Furthermore, the second reagent pipette 13 is supported capable of movement and rotational movement in the axial direction (vertical direction) and the horizontal direction of the reaction turntable 6 by the second reagent pipette driving mechanism not shown, in the same way as the first reagent pipette 12. Then, the second reagent pipette 13 makes a reciprocating motion between the second reagent turntable 5 and the reaction turntable 6.

The second reagent pipette 13 inserts the pipette into the second reagent container 25 of the second reagent turntable 5 and suctions a predetermined amount of the second reagent. Then; the second reagent pipette 13 discharges the suctioned second reagent into the reaction container 26 of the reaction turntable 6.

The dilution agitation device 9 and the dilution cleaning device 11 are arranged in the periphery of the dilution turntable 3. The dilution agitation device 9 inserts an agitator not shown into the dilution container 23 and agitates the sample and the dilution liquid.

The dilution cleaning device 11 is a device for cleaning the dilution container 23 after the dilution sample has been suctioned by the sampling pipette 8. This dilution cleaning device 11 has a plurality of dilution container cleaning nozzles. The plurality of dilution container cleaning nozzles is connected to a waste liquid pump not shown, and a cleanser pump not shown. The dilution cleaning device 11 inserts the dilution container cleaning nozzle into the dilution container 23 and suctions the dilution sample remaining in the dilution container 23 by the dilution container cleaning nozzle inserted by driving the waste liquid pump. Then, the dilution cleaning device 11 discharges the suctioned dilution sample into the waste liquid tank not shown.

After that, the dilution cleaning device 11 supplies a cleanser to the dilution container cleaning nozzle from the cleanser pump and discharges the cleanser into the dilution container 23 from the dilution container cleaning nozzle. The inside of the dilution container 23 is cleaned by this cleanser. After that, the dilution cleaning device 11 suctions the cleanser by the dilution container cleaning nozzle and dries the inside of the dilution container 23.

The first reaction agitating device 14, the second reaction agitating device 15, and the reaction container cleaning device 18 are arranged in the periphery of the reaction turntable 6. The first reaction agitating device 14 inserts the agitator, not shown, into the reaction container 26 and agitates the dilution sample and the first reagent. As a result, reaction between the dilution sample and the first reagent is uniformly and rapidly performed. Note that, since the configuration of the first reaction agitating device 14 is the same as that of the dilution agitating device 9, the explanation thereof is omitted here.

The second reaction agitating device 15 inserts the agitator, not shown, into the reaction container 26 and agitates the dilution sample, the first reagent, and the second reagent. As a result, the reaction among the dilution sample, the first reagent, and the second reagent is uniformly and rapidly preformed. Note that, since the configuration of the second reaction agitating device 15 is the same as that of the dilution agitating device 9, the explanation thereof is omitted here.

The reaction container cleaning device 18 is a device for cleaning the inside of the reaction container 26, of which an inspection is finished. This reaction container cleaning device 18 has a plurality of reaction container cleaning nozzles. The plurality of reaction container cleaning nozzles is connected to the waste liquid pump not shown, and the cleanser pump not shown, in the same way as the dilution container cleaning nozzle. Note that, since the cleaning process in the reaction container cleaning device 18 is the same as the aforementioned dilution cleaning device 11, the explanation thereof is omitted.

Furthermore, the multi-wavelength photometer 16 is arranged so as to face an outer wall of the reaction turntable 6 in the periphery of the reaction turntable 6. The multi-wavelength photometer 16 performs optical measurement on the dilution sample poured into the reaction container 26 and caused to react with a first chemical and a second chemical, outputs amounts of various components in the sample as numerical data as "absorbance" so as to thereby detect a reaction state of the dilution sample.

Furthermore, a constant-temperature bath not shown is arranged in the periphery of the reaction turntable 6. This constant-temperature bath is configured so as to hold a temperature of the reaction container 26 provided on the reaction turntable 6 constant at all times.

1-3. Configuration of Sample Rack Conveying Unit

Subsequently, detailed configuration of the sample rack conveying unit (hereinafter referred to simply as a "conveying unit") 30 will be described.

As illustrated in FIG. 1, the conveying unit 30 is arranged adjacent to the biochemical analyzing device 1. The conveying unit 30 supplies the sample container 21 to the sample turntable 2 and recovers the used sample container 21. Furthermore, the sample container 21 is accommodated in the sample rack 90. The sample rack 90 is constituted capable of accommodating a plurality of the sample containers 21 (five containers in this embodiment). Then, the conveying unit 30 conveys the sample rack 90 containing the sample container 21.

Note that a direction in parallel with the horizontal direction and where the conveying unit 30 and the biochemical analyzing device 1 are adjacent to each other is assumed to be a first direction X. Furthermore, a direction in parallel to the horizontal direction and orthogonal to the first direction X is assumed to be a second direction Y.

The conveying unit 30 has a plurality of supply trays 31 (three in this embodiment), a plurality of recovery trays 32 (three in this embodiment); a supply conveying portion 33, a recovery conveying portion 34, a container replacement portion 35, and a lane change portion 36.

The supply tray 31 is arranged on one side in the conveying unit 30 in the first direction X. The recovery tray 32 is arranged on the other side from the supply tray 31 in the first direction X. The supply tray 31 accommodates the sample container 21 to be supplied to the sample turntable 2 in a state of being accommodated in the sample rack 90. Then, the supply tray 31 sends out the sample rack 90 to the supply conveying portion 33.

The supply conveying portion 33 has a first conveying belt 41, a rotating mechanism 42, and a second conveying belt 43. The first conveying belt 41 conveys the sample rack 90 along the first direction X from the supply tray 31 to the rotating mechanism 42. The rotating mechanism 42 rotates the conveying direction of the sample rack 90 by substantially 90 degrees and conveys the sample rack 90 from the first conveying belt 41 to the second conveying belt 43. The second conveying belt 43 conveys the sample rack 90 along the second direction Y.

In addition, the container replacement portion 35 is provided in a middle portion of the second conveying belt 43. The container replacement portion 35 sends out the sample container 21 from the sample rack 90 conveyed from the second conveying belt 43 onto the sample turntable 2. Additionally, the container replacement portion 35 receives the used sample container 21 from the sample turntable 2 and accommodates the received sample container 21 to the sample rack 90 arranged on the second conveying belt 43.

Furthermore, the lane change portion 36 is provided on an end portion on the side opposite to the rotating mechanism 42 in the second conveying belt 43. The lane change portion 36 sends out the sample rack 90 conveyed by the second conveying belt 43 to the recovery conveying portion 34.

Furthermore, the supply conveying portion 33 has a supply-side sensor 44 for detecting the sample rack 90. The supply-side sensor 44 is arranged in the vicinity of the supply tray 31 in the first conveying belt 41.

The recovery conveying portion 34 conveys the sample rack 90 received from the lane change portion 36 to the recovery tray 32. Note that a detailed configuration of the recovery conveying portion 34 will be described later. Then, the recovery tray 32 accommodates the sample rack 90 conveyed by the recovery conveying portion 34.

Subsequently, the detailed configuration of the recovery conveying portion 34 will be described by referring to FIGS. 2 to 6.

Figure 2:
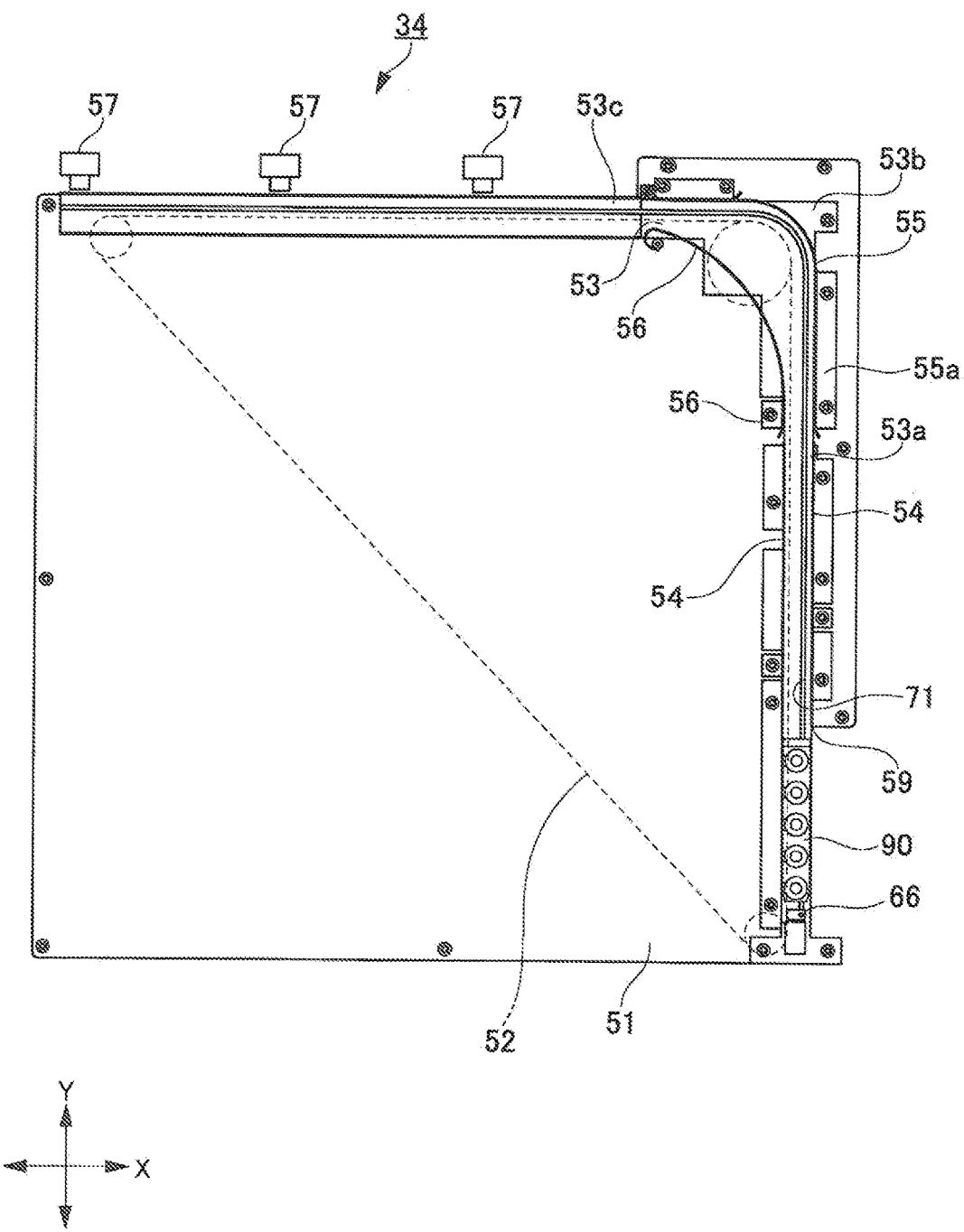
FIG. 2 is a plan view illustrating a sample rack conveying unit according to the exemplary embodiment of the present invention.
Figure 3:
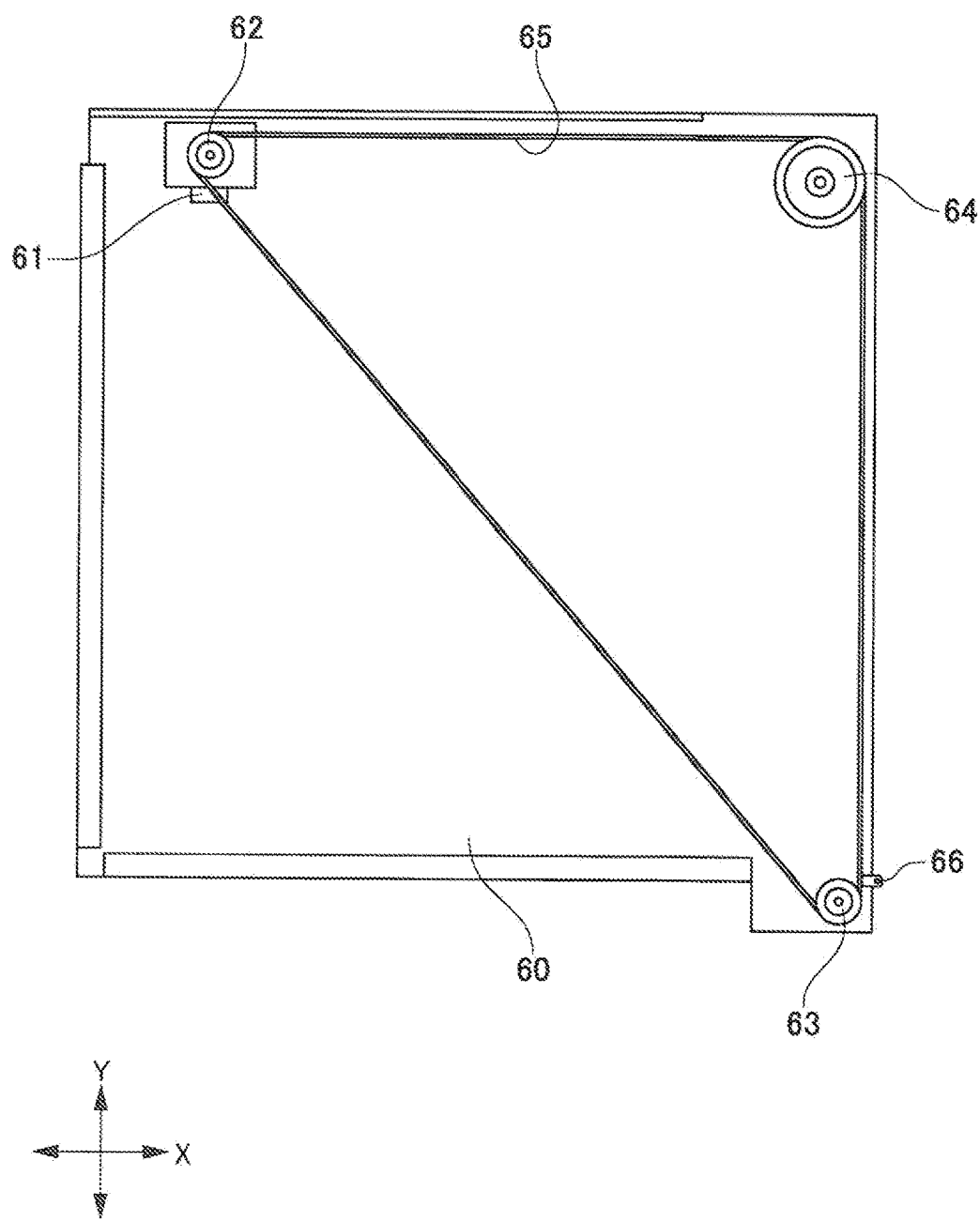
FIG. 3 is a plan view illustrating a driving portion of the sample rack conveying unit according to the exemplary embodiment of the present invention.
Figure 4:
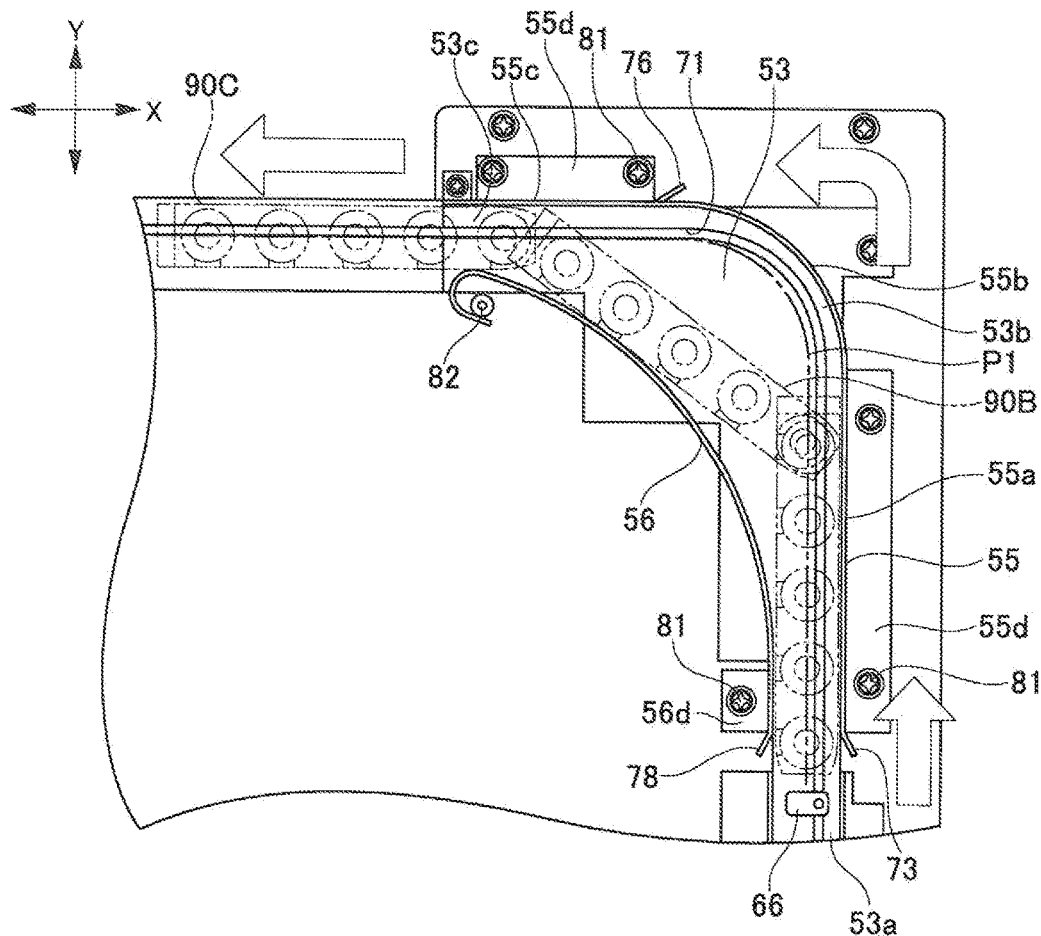
FIG. 4 is a plan view illustrating an essential part of the sample rack conveying unit according to the embodiment of the present invention in an enlarged manner.

FIG. 2 is a plan view illustrating the recovery conveying portion 34. FIG. 3 is a plan view illustrating a driving mechanism 52 which will be described later, and FIG. 4 is a plan view illustrating an essential part of the recovery conveying portion 34 in an enlarged manner.

As illustrated in FIG. 2, the recovery conveying portion 34 changes the conveying direction of the sample rack 90 substantially 90 degrees from the second direction Y to the first direction X and conveys the sample rack 90. The recovery conveying portion 34 has a base plate 51, a driving mechanism 52, a sliding rail plate 53, a plurality of straight guide plates 54, a first guide plate 55, a second guide plate 56, and a recovery-side sensor 57. The recovery-side sensor 57 is arranged in the vicinity of the recovery tray 32 and detects the conveyed sample rack 90.

The base plate 51 is formed in a flat plate shape. Furthermore, in the base plate 51, an opening portion 51a is formed along the conveying direction of the sample rack 90 (refer to FIG. 6). The sliding rail plate 53, the plurality of straight guide plates 54, the first guide plate 55, and the second guide plate 56 are fixed to one surface of the base plate 51 through fixing screws 81. Moreover, the driving mechanism 52 is arranged on the other surface on the side opposite to the one surface of the base plate 51.

The sliding rail plate 53 is formed in a flat plate shape. Then, the sample rack 90 slides on the sliding rail plate 53. The sliding rail plate 53 has a first straight portion 53a extending along the second direction Y, a curved portion 53b which continues to the first straight portion 53a and in which a moving direction of the sample rack 90 changes from the second direction Y to the first direction X, and a second straight portion 53c continuing to the curved portion 53b and extending in the first direction X.

In addition, in the sliding rail plate 53, a groove portion 71 is formed along a track on which the sample rack 90 is conveyed (hereinafter referred to as a "conveying track"). The groove portion 71 is formed linearly along the second direction Y in the first straight portion 53a and is curved at a predetermined radius in the curved portion 53b. Furthermore, the groove portion 71 is formed linearly along the first direction X in the second straight portion 53c.

As illustrated in FIG. 4, the groove portion 71 formed in the first straight portion 53a and the curved portion 53b is arranged closer to an outer side of the conveying track in a radial direction than a center line P1 of the sample rack 90 sliding on the sliding rail plate 53 in a width direction. Then, a presser 66 of the driving mechanism 52 which will be described later passes through this groove portion 71.

Note that a portion on which the groove portion 71 is formed is not limited to the above, but is set as appropriate along the conveying track of the sample rack 90.

A plurality of the straight guide plates 54 is arranged on the first straight portion 53a in the sliding rail plate 53. The plurality of straight guide plates 54 is arranged on both sides of the sliding rail plate 53 in the first direction X. However, the straight guide plate 54 is not arranged on one side in the first straight portion 53a of the sliding rail plate 53 in the second direction Y, that is, on the other side of the first direction X on the side opposite to the curved portion 53b. Then, this portion where the straight guide plate 54 is not arranged serves as a receiving port 59 for receiving the sample rack 90 from the lane change portion 36 (refer to FIG. 1).

FIG. 3 is a plan view illustrating the driving mechanism 52.

As illustrated in FIG. 3, the driving mechanism 52 has a driving portion 61, a driving pulley 62, a first driven pulley 63, a second driven pulley 64, a driving belt 65, and the presser 66. This driving mechanism 52 is arranged on a flat-plate shaped driving base portion 60.

The driving portion 61 and the driving pulley 62 are arranged on one side in the first direction X and on the other side in the second direction Y. In this embodiment, for example, a stepping motor is used for the driving portion 61. The driving pulley 62 is connected to a driving shaft, not shown, of the driving portion 61. A rotational shaft of the driving pulley 62 is provided on a plane formed by the first direction X and the second direction Y, that is, substantially perpendicularly to the horizontal direction. Then, the driving pulley 62 is rotated when the driving portion 61 is driven.

The first driven pulley 63 is arranged on the other side in the first direction X and on one side in the second direction Y. Namely, the first driven pulley 63 is arranged in the vicinity of the receiving port 59 of the recovery conveying portion 34 (refer to FIG. 2). The second driven pulley 64 is arranged on the other side in the first direction X and on the other side in the second direction Y. That is, the second driven pulley 64 is arranged in the vicinity of the curved portion 53b of the sliding rail plate 53 (refer to FIG. 2). The first driven pulley 63 and the second driven pulley 64 are rotatably supported by the driving base portion 60.

The driving belt 65 is formed endlessly. The driving belt 65 is stretched across the driving pulley 62, the first driven pulley 63, and the second driven pulley 64. A portion passing from the first driven pulley 63 to the driving pulley 62 via the second driven pulley 64 in the driving belt 65 is arranged below the groove portion 71 in the sliding rail plate 53.

Figure 6:
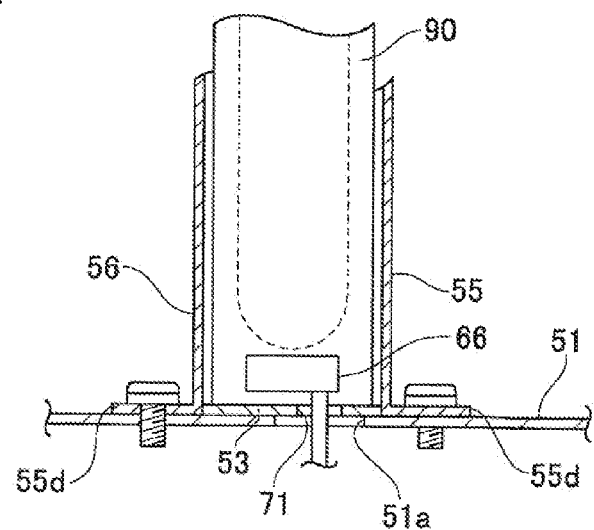
FIG. 6 is a cross-sectional view of FIG. 4 illustrating the sample rack conveying unit according to the exemplary embodiment of the present invention.

In addition, the presser 66 is fixed to the driving belt 65. As illustrated in FIG. 6, the presser 66 penetrates the opening portion 51a of the base plate 51 and the groove portion 71 of the sliding rail plate 53.

When the driving portion 61 is driven, the driving pulley 62, the first driven pulley 63, and the second driven pulley 64 are rotated. Then, the driving belt 65 moves among the driving pulley 62, the first driven pulley 63, and the second driven pulley 64. Accordingly, the presser 66 fixed to the driving belt 65 moves together with the driving belt 65 from the first driven pulley along the groove portion 71 in the sliding rail plate 53, to the driving pulley 62 via the second driven pulley 64. Then, the presser 66 presses the sample rack 90 placed on the sliding rail plate 53. As a result, the sample rack 90 slides on the sliding rail plate 53 and is conveyed to a predetermined position by the presser 66.

Note that, in this embodiment, the number of the driven pulleys is set to two, but this is not limiting, and three or more driven pulleys may be provided in accordance with the conveying track of the sample rack 90.

Subsequently, the first guide plate 55 and the second guide plate 56 will be described.

As illustrated in FIG. 4, the first guide plate 55 and the second guide plate 56 are arranged on the curved portion in which the conveying direction changes on the conveying track of the sample rack 90. Namely, the first guide plate 55 and the second guide plate 56 are arranged on the curved portion 53b of the sliding rail plate 53.

The first guide plate 55 is arranged on an outer side of the conveying track in the radial direction, and the second guide plate 56 is arranged on an inner side of the conveying track in the radial direction. Furthermore, the first guide plate 55 is arranged on the outer side than the center line P1 only by a distance of a half of the length of the sample rack 90 in the width direction. The sample rack 90 sliding on the sliding rail plate 53 is brought into contact with the first guide plate 55 and the second guide plate 56. Then, the first guide plate 55 and the second guide plate 56 guide conveyance of the sample rack 90.

Figure 5:
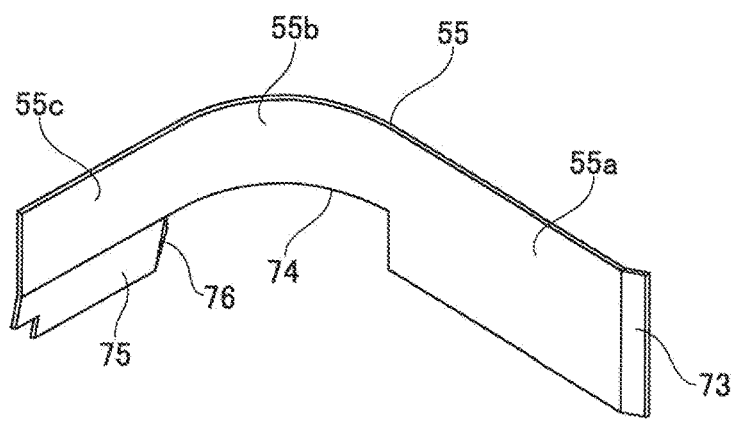
FIG. 5 is a perspective view illustrating a first guide plate in the sample rack conveying unit according to the exemplary embodiment of the present invention.

FIG. 5 is a perspective view illustrating the first guide plate 55.

As illustrated in FIG. 5, the first guide plate 55 is a partially curved flat-plate shaped member. The first guide plate 55 has a first plane 55a, a curved surface 55b continuing to the first plane 55a, and a second plane 55c continuing to the curved surface 55b. The first plane 55a is arranged on an upstream side of the conveying tack and the second plane 55c is arranged on a downstream side of the conveying track. The first plane 55a, the curved surface 55b, and the second plane 55c are installed upright upward in the vertical direction when the first guide plate 55 is fixed to the base plate 51.

As illustrated in FIGS. 4 and 5, a guide piece 73 is provided on the upstream side of the conveying track on the first plane 55a. The guide piece 73 is bent toward an outer side of the conveying track from the first plane 55a.

Furthermore, as illustrated in FIG. 5, a notch 74 is formed in a lower part of the curved surface 55b in the vertical direction. Furthermore, an inclined piece 75 is provided in a lower part of the second plane 55c in the vertical direction. The inclined piece 75 is inclined toward the outer side of the conveying track from the second plane 55c. Furthermore, a call-in piece 76 is provided at an end portion on the upstream side of the conveying track of the inclined piece 75.

As illustrated in FIG. 4, the first guide plate 55 has a fixing piece 55d bent substantially perpendicularly from a part of lower ends of the first plane 55a and the second plane 55c in the vertical direction. Then, the fixed piece 55d is fastened and fixed to the base plate 51 via the fixing screw 81.

A material excellent in abrasion resistance and with high rigidity is favorable for a material for the first guide plate 55, since the material is brought into contact with the sample rack 90.

The second guide plate 56 is a partially curved flat-plate shaped member. A guide piece 78 is provided on the upstream side of the conveying track in the second guide plate 56 in the same way as the first guide plate 55. Then, the sample rack 90 conveyed by the presser 66 is guided between the first guide plate 55 and the second guide plate 56 by the guide piece 73 of the first guide plate 55 and the guide piece 78 of the second guide plate 56.

Moreover, the second guide plate 56 is formed of a member having elasticity. The second guide plate 56 is constituted of, for example, a leaf spring. An elastic force of the second guide plate 56 is set smaller than the pressing force of the presser 66 in the driving mechanism 52 against the sample rack 90.

A fixed piece 56d to be fastened and fixed onto the base plate 51 is provided on the upstream side of the conveying track of the second guide plate 56. An end portion on the upstream side of the conveying track in the second guide plate 56 is fixed to the base plate 51. In contrast to this, an end portion on the downstream side of the conveying track in the second guide plate 56 is only in contact with a retaining pin 82. Accordingly, the end portion on the downstream side of the conveying track in the second guide plate 56 is movable at a predetermined interval in the horizontal direction and is urged by the elastic force toward the first guide plate 55.

Furthermore, the interval on the downstream side of the conveying track in the first guide plate 55 and the second guide plate 56 is set smaller than the interval on the upstream side of the conveying track. Note that the interval on the upstream side of the conveying track in the first guide plate 55 and the second guide plate 56 is set substantially equal to or slightly larger than the length of the sample rack 90 in the width direction.

FIG. 6 is a cross-sectional view illustrated in FIG. 4.

As illustrated in FIG. 6, in the first guide plate 55 and the second guide plate 56, the respective fixing pieces 55d and 56d are brought into contact with a side end portion of the sliding rail plate 53 when the first guide plate 55 and the second guide plate 56 are mounted on the base plate 51. Furthermore, the plurality of straight guide plates 54 is also brought into contact with the side end portion of the sliding rail plate 53 when the plurality of straight guide plates 54 is mounted on the base plate 51. As a result, positioning with respect to the base plate 51 in the first guide plate 55, the second guide plate 56, and the plurality of straight guide plates 54 can be easily carried out.

2. Operation of Recovery Conveying Portion in Sample Rack Conveying Unit

Subsequently, an operation of the recovery conveying portion having the aforementioned configuration will be described by referring to FIGS. 2, 4, and 7 to 9.

Figure 7:
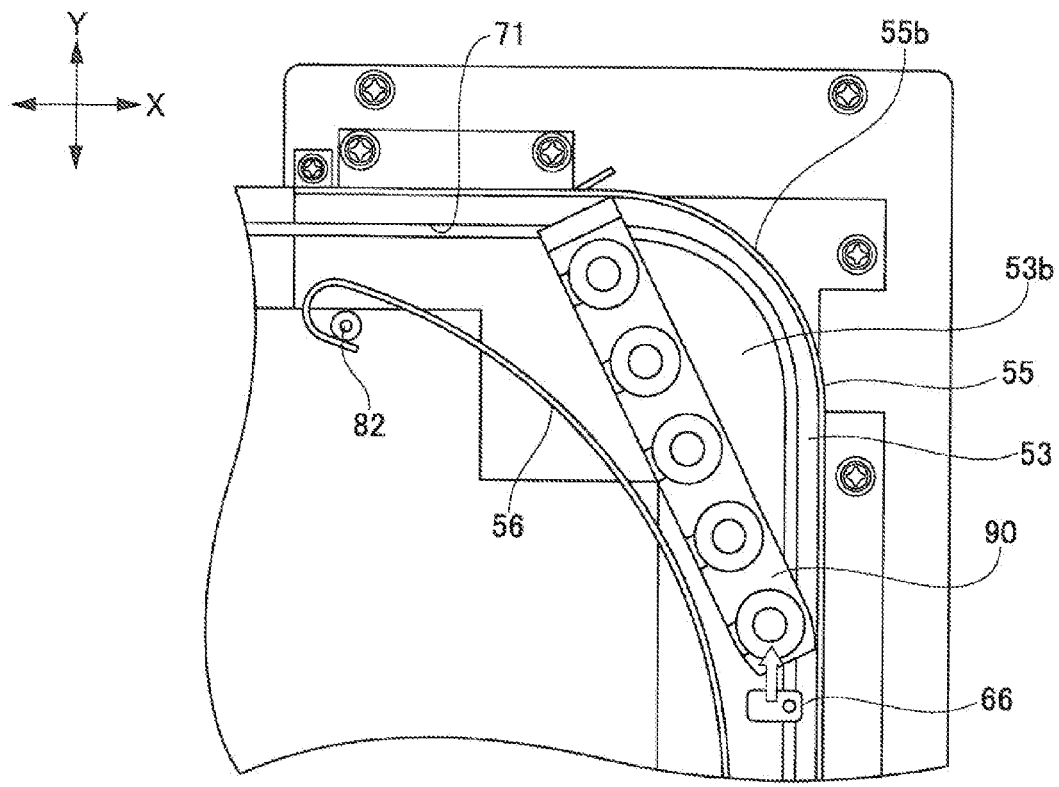
FIG. 7 is a plan view illustrating a conveyance state of the sample rack in the sample rack conveying unit according to the embodiment of the present invention.
Figure 8:
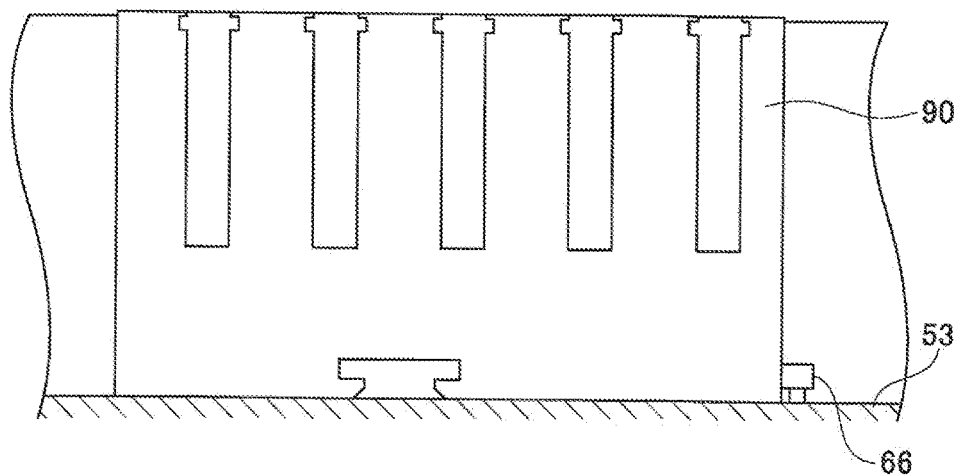
FIG. 8 is a side view illustrating the conveyance state of the sample rack in the sample rack conveying unit according to the exemplary embodiment of the present invention.
Figure 9:
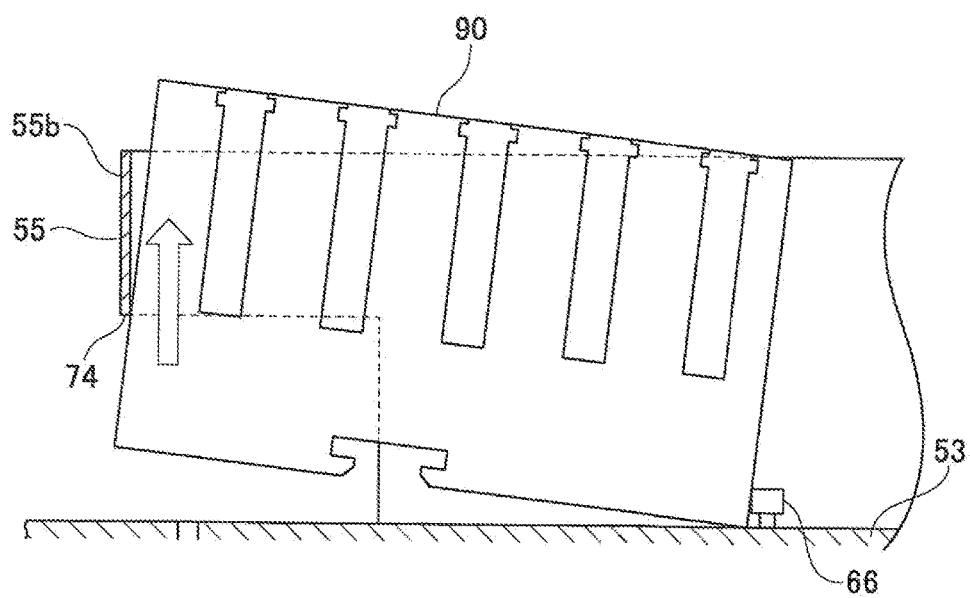
FIG. 9 is a side view illustrating an essential part of the conveyance state of the sample rack in the sample rack conveying unit according to the exemplary embodiment of the present invention.

FIG. 7 is a plan view illustrating an essential part of the conveyed state of the sample rack 90 in an enlarged manner, FIG. 8 is a side view illustrating the conveyed state of the sample rack 90, and FIG. 9 is a side view illustrating the essential part of the conveyed state of the sample rack 90 in an enlarged manner.

As illustrated in FIG. 2, when the sample rack 90 is conveyed from the receiving port 59 onto the sliding rail plate 53, the recovery conveying portion 34 drives the driving mechanism 52. At this time, the presser 66 is arranged on the upstream side from the conveying track of the sample rack 90. When the driving portion 61 of the driving mechanism 52 is driven, the driving belt 65 is rotated, and the presser 66 fixed to the driving belt 65 is moved along the groove portion 71 of the sliding rail plate 53. As a result, the sample rack 90 is pressed by the presser 66 and is made to slide along the second direction Y on the first straight portion 53a of the sliding rail plate 53.

As illustrated in FIG. 4, the sample rack 90 is guided by the guide piece 73 of the first guide plate 55 and the guide plate 78 of the second guide plate 56 and is inserted between the first guide plate 55 and the second guide plate 56. Furthermore, the sample rack 90 is pressed by the presser 66 and is conveyed to the curved portion 53b of the sliding rail plate 53, by rotating the driving belt 65.

As illustrated in FIG. 7, a corner portion in front of the sample rack 90 in the conveying direction and on the outer side of the curved portion of the conveying track in the radial direction is brought into contact with the curved surface 55b of the first guide plate 55. As illustrated in FIG. 4, the groove portion 71 is arranged on the outer side of the conveying track in the radial direction from the center line P1 of the sample rack 90 in the width direction sliding on the sliding rail plate 53. Then, the presser 66 presses the outer side of the conveying track in the radial direction from the center line P1 in the sample rack 90. Namely, the presser 66 presses the sample rack 90 by shifting a dead point when the sample rack 90 rotates. As a result, the sample rack 90 can be prevented from being sandwiched between the presser 66 and the first guide plate 55, whereby the conveying direction of the sample rack 90 can be smoothly changed.

Furthermore, as illustrated in FIG. 8, the presser 66 presses the lower part of the sample rack 90 in the horizontal direction. Furthermore, the sample rack 90 is rubbed by the curved surface 55b (refer to FIG. 7) of the first guide plate 55. Accordingly, a direction of a moment of a frictional force generated when the sample rack 90 is moved is directed upward in the vertical direction. Therefore, as illustrated in FIG. 9, there is a risk that the sample rack 90 floats. Then, by floating of the sample rack 90, a corner portion on a lower side of the sample rack 90 in the vertical direction moves to the outer side of the conveying track from the curved surface 55b of the first guide plate 55. As a result, there is a risk that the corner portion of the sample rack 90 is caught by the first guide plate 55.

In contrast to this, in this embodiment, the notch 74 is formed on the curved surface 55b of the first guide plate 55, and furthermore, the call-in piece 76 and the inclined piece 75 (refer to FIG. 5) are provided on the second plane 55c arranged on the downstream side of the curved surface 55b. Accordingly, even if the sample rack 90 floats at the curved portion, its corner portion can be prevented from being caught by the first guide plate 55. As a result, the sample rack 90 can be smoothly conveyed.

When the sample rack 90 is further pressed from the state illustrated in FIG. 7, the sample rack 90 is separated from the first guide plate 55 and is brought into contact with the second guide plate 56 arranged on an inner side in the radial direction, in the same way as a sample rack 90B illustrated in FIG. 4. Then, the presser 66 moves along the groove portion 71 and presses the sample rack 90. As a result, the sample rack 90 is rotated, and the conveying direction of the sample rack 90 is changed from the second direction Y to the first direction X.

Furthermore, the second guide plate 56 urges the sample rack 90 toward the first guide plate 55 side. As a result, the sample rack 90 is put into a state of being directed to the first direction X illustrated in FIG. 4. As described above, the sample rack 90 having passed through the curved portion can be conveyed toward the same position at all times, by urging the sample rack 90 toward the first guide plate 55 side by the second guide plate 56.

Note that the elastic force of the second guide plate 56 is set smaller than the pressing force of the presser 66 in the driving mechanism 52 against the sample rack 90, and thus the sample rack 90 can be prevented from being sandwiched between the second guide plate 56 and the first guide plate 55.

Furthermore, the sample rack 90 is conveyed along the first direction X by further pressing the sample rack 90 by the presser 66. Then, the recovery-side sensor 57 (refer to FIG. 2) detects the sample rack 90 to thereby be able to convey the sample rack 90 to a predetermined position. When the conveyance is finished, the driving mechanism 52 drives the driving portion 61 in a direction opposite to that at the time of conveyance. Then, the driving pulley 62, the first driven pulley 63, the second driven pulley 64, and the driving belt 65 are rotated in the direction opposite to that at the time of conveyance. As a result, the presser 66 fixed to the driving belt 65 returns to the vicinity of the receiving port 59 illustrated in FIG. 2 along the groove portion 71. As a result, the operation of the recovery conveying portion 34 is completed.

According to the recovery conveying portion 34 of this embodiment, three operations, that is, the straight movement of the sample rack 90 along the second direction Y, the rotational movement from the second direction Y to the first direction X, and furthermore, the straight movement along the first direction X can be performed by one driving portion 61. As a result, the number of driving portions can be reduced, and thus cost reduction can be realized. Furthermore, the mechanism for conveying the sample rack 90 can be simplified.

Furthermore, the sample rack 90 having passed through the curved portion can be arranged at the same position at all times, by urging the sample rack 90 having passed through the curved portion by the second guide plate 56, toward the first guide plate 55 side. As a result, an operation failure caused by a change in the position of the sample rack 90 can be prevented, whereby the sample rack 90 can be stably conveyed.

Here, in the prior-art technology, since two conveyers for linearly advancing the sample rack 90 and a disc for converting the conveying direction are provided, heights in the vertical direction of the two conveyers and the disc are required to be aligned. However, it is difficult to solve the discrepancy in the height direction between the two conveyers and the disc, and a slight level difference is generated between the conveyers and the disk. As a result, there is a risk that the sample rack 90 is caught by this slight level difference or the sample drops from the sample container accommodated in the sample rack 90.

In contrast to this, in this embodiment, the sample rack 90 slides on one sliding rail plate 53 at all times when the rack is linearly advancing or rotating. As a result, time and trouble for positioning in the height direction can be saved, and a level difference when the sample rack 90 moves can be solved, whereby the sample rack 90 can be stably conveyed.

Note that the present invention is not limited to the embodiment described above and illustrated in the drawings but is capable of various modifications within a range not departing from the gist of the invention described in claims. For example, in the aforementioned exemplary embodiment, the example in which the configuration of the present invention is applied to the recovery-side conveying portion has been described, but this is not limiting, and the example may be applied to the supply-side conveying portion.

Note that, in the aforementioned exemplary embodiment, the example in which the presser presses the lower part of the sample rack has been described, but this is not limiting, and the presser may be configured to press an upper part of the sample rack in the vertical direction. In this case, the notch and the inclined portion formed in the first guide plate is preferably provided in the upper part in the vertical direction.

Furthermore, the example in which the conveying direction of the sample rack is converted by substantially 90 degrees from the second direction Y to the first direction X has been described but the angle by which the conveying direction of the sample rack is converted is not limited to that. The angle by which the conveying direction of the sample rack is converted is variously set depending on the device, and the conveying direction of the sample rack may be converted by the angle of 90 degrees or more, or less than 90 degrees.

Moreover, an example of an application to a biochemical analyzing device used for analyzing a biological specimen such as blood or urine, as the automatic analyzing device, has been described, but this is not limiting, and application to a device for analyzing a water quality, food or any other various substances is possible.

PARTIAL REFERENCE SIGNS LIST

1 biochemical analyzing device (automatic analyzing device)
30 sample rack conveying unit
31 supply tray
32 recovery tray
33 supply conveying portion
34 recovery conveying portion
35 container replacement portion
36 lane change portion
51 base plate
51*a* opening portion
52 driving mechanism
53 sliding rail plate
53*a* first straight portion
53*b* curved portion
53*c* second straight portion
54 straight guide plate
55 first guide plate
55*a* first plane
55*b* curved surface
55*c* second plane
55*d* fixing piece
56 second guide plate
56*d* fixing piece
57 recovery-side sensor
59 receiving port
60 driving base portion
61 driving portion
62 driving pulley
63 first driven pulley
64 second driven pulley
65 driving belt
66 presser
71 groove portion
73, 78 guide piece
75 inclined piece
76 call-in piece
90 sample rack
100 biochemical analysis system (automatic analysis system)
P1 center line

Having thus described my invention with the detail and particularity required by the Patent Laws, what is desired protected by Letters Patent is set forth in the following claims.

The invention claimed is:

1. A sample rack conveying unit comprising:
   a sample rack including a plurality of openings, each opening configured to hold a sample container;
   a sliding rail plate on which the sample rack accommodating the sample container slides and is conveyed and in which a groove portion is formed along a conveying track along which the sample rack is conveyed;
   a presser passing through the groove portion for pressing the sample rack so as to slide and be conveyed:
   an endless driving belt on which the presser is mounted;
   a plurality of pulleys among which the driving belt is extended; a driving portion for rotationally driving the plurality of pulleys to move the driving belt and thereby moving the presser to press the sample track so as to slide and be conveyed:
a first guide plate that is arranged, upright in a vertical direction, on an outer side of a curved portion of the conveying track in a radial direction thereof where a direction of the conveying track along which the sample rack is conveyed changes and that guides conveyance of the sample rack; and
a second guide plate that is arranged, upright in the vertical direction, on an inner side of the curved portion of the conveying track in the radial direction thereof and that guides conveyance of the sample rack,
wherein a notch is formed in a lower vertical surface part of the first guide plate and the notch is configured to receive the corner of the sample rack if the rack lifts up at the curved portion of the conveying track so that the sample rack does not get jammed.

2. The sample rack conveying unit according to claim 1, wherein
the groove portion formed along the curved portion of the conveying track is formed on the outer side of the curved portion of the conveying track in the radial direction thereof from a center of the sample rack in a width direction thereof; and
the presser presses an outer side of the sample rack in the radial direction of the conveying track from the center of the sample rack in the width direction thereof, in the curved portion of the conveying track.

3. The sample rack conveying unit according to claim 1, wherein
the second guide plate has elasticity and urges the sample rack toward the first guide plate.

4. The sample rack conveying unit according to claim 1, further comprising:
a base plate to which the sliding rail plate, the first guide plate, and the second guide plate are fixed, wherein
at least a part of the first guide plate and the second guide plate is brought into contact with a side end portion of the slide rail plate.

5. An automatic analysis system comprising:
an automatic analyzing device for analyzing a sample accommodated in a sample container; and
a sample rack including a plurality of openings, each opening configured to hold a sample container;
a sample rack conveying unit for conveying the sample rack in which the sample container is accommodated, wherein
the sample rack conveying unit includes:
a sliding rail plate on which a sample rack accommodating a sample container slides and is conveyed and in which a groove portion is formed along a conveying track along which the sample rack is conveyed;
a presser passing through the groove portion and pressing the sample rack so as to slide and be conveyed:
an endless driving belt on which the presser is mounted;
a plurality of pulleys among which the driving belt is extended;
a driving portion for rotationally driving the plurality of pulleys to move the driving belt and thereby moving the presser to press the sample track so as to slide and be conveyed:
a first guide plate that is arranged, upright in a vertical direction, on an outer side of a curved portion of the conveying track in a radial direction thereof where a direction of the conveying track along which the sample rack is conveyed changes and that guides conveyance of the sample rack; and
a second guide plate that is arranged, upright in the vertical direction, on an inner side of the curved portion of the conveying track in the radial direction thereof and that guides conveyance of the sample rack,
wherein a notch is formed in a lower vertical surface part of the first guide plate and the notch is configured to receive the corner of the sample rack if the rack lifts up at the curved portion of the conveying track so that the sample rack does not get jammed.

\* \* \* \* \*